United States Patent
Sloane et al.

(10) Patent No.: US 7,326,679 B2
(45) Date of Patent: Feb. 5, 2008

(54) ANTICANCER PEPTIDE COMPOSITIONS

(75) Inventors: Nathan H. Sloane, Germantown, TN (US); Kathleen M. Hehir, Grafton, MA (US); Alexander Baguisi, Grafton, MA (US); Paul DiTullio, Northboro, MA (US)

(73) Assignee: TranXenoGen, Inc., Northboro, MA (US)

( * ) Notice: Subject to any disclaimer, the term of this patent is extended or adjusted under 35 U.S.C. 154(b) by 0 days.

(21) Appl. No.: 10/977,629

(22) Filed: Oct. 29, 2004

(65) Prior Publication Data

US 2005/0239703 A1 Oct. 27, 2005

Related U.S. Application Data

(60) Provisional application No. 60/547,124, filed on Feb. 24, 2004, provisional application No. 60/515,861, filed on Oct. 30, 2003.

(51) Int. Cl.
*A61K 38/10* (2006.01)
(52) U.S. Cl. .......................................... 514/2
(58) Field of Classification Search ............... None
See application file for complete search history.

(56) References Cited

U.S. PATENT DOCUMENTS 6,864,356 B2 * 3/2005 Sloane ..................... 530/326

OTHER PUBLICATIONS

Zheng et al., "Control of Stromal Keratitis by Inhibition of Neovascularization," 2001, Journal of Pathology, 159, 1021-9.*
Ginalski et al. "Practical lessons from protein structure prediction." Nuc. Ac. Res., 2005, 33, 1874-1891.*
Rudinger "Characteristic of the amino acids as components of a peptide hormone sequence." (Peptide Hormones (Ed. J.A. Parson). University Park Press. Baltimore, 1976, pp. 1-7.*
Pitt et al. "Single amino acid substitution mutants of Klebsiella pneumoniae singma54 defective in transcription" Nuc. Ac. Res., 2000, 28, 4419-4427.*
Bradley et al. "Limits of Cooperativity in a Structurally Modular Protein: Response of the Notch Ankyrin Domain to Analogous Alanine Substitutions in Each Repeat" J. Mol. Biol., 2002, 324, 373-386.*
Flanagan et al. "Truncated staphyloccal nuclease is compact but disordered" Proc. Natl. Acad. Sci. USA, 1992, 89, 748-752.*
Sawai et al. "Impact of single-residue mutations on the structure and function of ovispirin/novispirin antimicrobal peptides" Prot. Engin., 2002, 15, 225-232.*
Schnog et al. "Sickle cell disease; a general overview" J. Med., 2004, 62, 364-374.*
Arap et al. *Science*, 279:377-380 (1998).
Baguisi et al. *Theriogenology*, 51(1):162 (1999).
Bergers et al. *Science*, 284:808-812 (1999).
Fidler et al. *Cell*, 79(2):185-188 (1994).
Folkman *Nat. Med.*, 1(1):27-31 (1995).
Hehir et al. *Peptides*, 25:543-549 (2004).
Homandberg et al. *Am. J. Pathol.*, 120(3):327-332 (1985).
Homandberg et al. *Biochim. Biophys. Acta*, 874:61-71 (1986).
Masood et al. *Blood*, 93(3):1038-1044 (1999).
Mayo et al. *J. Biol. Chem.*, 278(46):45746-45752 (2003).
O'Reilly et al. *Cell*, 79(2):315-328 (1994).
O'Reilly et al. *Cell*, 88(2):277-285 (1997).
O'Reilly et al. *Science*, 285:1926-1928 (1999).
Pottathil et al. *Cancer Res. Ther. Control*, 1:193-198 (1990).
Ridge et al. *Cytokine*, 8(1):1-5 (1996).
Sloane et al. *Biochem. J.*, 234(2):355-362 (1986).
Sloane et al. *Cancer Res. Ther. Control*, 3(1):49-52 (1992).
Sloane et al. *Tumor Targeting*, 2:322-326 (1996).

* cited by examiner

*Primary Examiner*—Cecilia J. Tsang
*Assistant Examiner*—Christina M Brady
(74) *Attorney, Agent, or Firm*—Ingrid A. Beattie; Mintz, Levin, Cohn, Ferris, Glovsky and Popeo, P.C.

(57) ABSTRACT

The invention provides compositions and methods for inhibiting angiogenesis associated with tumors and reducing tumor growth.

9 Claims, 9 Drawing Sheets

SEQUENCE LISTING

<160> NUMBER OF SEQ ID NOS: 4

<210> SEQ ID NO 1
<211> LENGTH: 20
<212> TYPE: PRT
<213> ORGANISM: Artificial sequence
<220> FEATURE:
<223> OTHER INFORMATION: chemically synthesized

<400> SEQUENCE: 1

Glu Leu Lys Cys Tyr Thr Cys Lys Glu Pro Met Thr Ser Ala Ser Cys
1               5                   10                  15

Arg Thr Ile Thr
            20

<210> SEQ ID NO 2
<211> LENGTH: 20
<212> TYPE: PRT
<213> ORGANISM: Artificial sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 2

Glu Leu Lys Cys Tyr Thr Cys Lys Glu Pro Met Thr Ser Ala Ser Cys
1               5                   10                  15

Arg Thr Ile Thr
            20

<210> SEQ ID NO 3
<211> LENGTH: 20
<212> TYPE: PRT
<213> ORGANISM: Artificial sequence
<220> FEATURE:
<223> OTHER INFORMATION: chemically synthesized

<400> SEQUENCE: 3

Glu Leu Lys Cys Tyr Thr Cys Lys Glu Pro Met Thr Ser Ala Ala Cys
1               5                   10                  15

Arg Thr Ile Thr
            20

<210> SEQ ID NO 4
<211> LENGTH: 20
<212> TYPE: PRT
<213> ORGANISM: Artificial sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 4

Glu Leu Lys Cys Tyr Thr Cys Lys Glu Pro Met Thr Ser Ala Ala Cys
1               5                   10                  15

Arg Thr Ile Thr
            20

ANTICANCER PEPTIDE COMPOSITIONS

RELATED APPLICATIONS

This invention claims priority to provisional patent application U.S. Ser. No. 60/547,124, filed on Feb. 24, 2004 and to provisional patent application U.S. Ser. No. 60/515,861, filed on Oct. 30, 2003, the entire contents of each of which are hereby incorporated by reference.

BACKGROUND OF THE INVENTION

The invention relates to cancer therapy.

Cancer is a disease manifested by uncontrolled cell growth that presents over 100 distinct clinical pathologies. The development of an effective therapy for such a broad spectrum of disease states represents a unique scientific challenge. Chemotherapeutic agents and radiation, which cause DNA mutations in actively dividing cells, were intended to selectively kill the cancer cells while not effecting normal cells. Unfortunately, these cytotoxic agents, while effective in managing several types of cancer, were limited in their utility due to adverse side effects and lack of specificity for cancer cells. Advancement in our understanding of cell biology and cancer has lead to the advent of new more selective treatments providing hope for cancer patients.

Recent clinical investigations have shown the benefit of combination therapies that target not only the cancer, but its ability to stimulate new blood vessel growth. Angiogenesis, new blood vessel formation, is critical for neoplastic growth and metastasis but is essentially quiescent in adults (I. J. Fidler, L. M. Ellis, Cell, 79, 185 (1994); J. Folkman, Nature Med. 1, 27, (1995)). A number of angiostatic factors such as endostatin (M. S. O'Reilly et. al., Cell 79, 315 (1994)) angiostatin (5. M. S. O'Reilly et. al., Cell 88, 277 (1997)), and thrombospondin have been identified and act to block various steps in the pathway. However, difficulties encountered in production, lack of specificity, and activity levels have combined to detract from the clinical utility of many of these factors.

SUMMARY OF THE INVENTION

The invention is based on the discovery that the N-terminal domain of antineoplastic urinary protein (ANUP) mediates anti-angiogenic activity. Accordingly, the invention provides an isolated composition containing an antineoplastic urinary protein polypeptide, which is at least 20 amino acids in length and includes the amino acid sequence of SEQ ID NO:1, 2, 3, or 4 as well as a method of inhibiting blood vessel formation in a tissue by contacting a bodily tissue, e.g., a tissue containing a tumor cell, with the polypeptide. The polypeptide is synthetic or recombinantly made. Preferably, the polypeptide is less than the full length naturally-occurring ANUP. The peptide contains amino acids 2-20, 3-20, 4-20, 5-20, 6-20, 7-20, 8-20, or 9-20 of SEQ ID NO:1 or 3. In another example, the peptide is a fragment of SEQ ID NO:1 or 3 and contains residues 5-10 of SEQ ID NO:1. For example, the polypeptide is at least 5 amino acids in length and is less than 80 amino acids in length, less than 75 amino acids, less than 70 amino acids, less than 60 amino acids, less than 50 amino acids, less than 40 amino acids, less than 30 amino acids, less than 25 amino acids, less than 20 amino acids, less than 19 amino acids, less than 15 amino acids, or less than 10 amino acids. For example, the peptide is a 6 mer (, residues 5-10 of SEQ ID NO:1) Preferably, the polypeptide inhibits blood vessel formation. In some embodiments, the polypeptide inhibits blood vessel formation and does not inhibit cell, e.g., tumor cell, proliferation directly but via inhibition of the developing blood vessels. Tumor burden, e.g., as evaluated by measuring tumor size or volume or number of tumors, is reduced in subjects treated with ANUP peptides described herein.

The peptides described herein are substantially pure. By a substantially pure polypeptide is meant that a polypeptide is isolated from those components (proteins and other naturally-occurring organic molecules) which naturally accompany it. A polypeptide is substantially pure when it constitutes at least 60%, by weight, of the protein in the preparation. Preferably, the protein in the preparation is at least 75%, more preferably at least 90%, and most preferably at least 99%, by weight, of the desired peptide. A substantially pure polypeptide is obtained, e.g., by extraction from a natural source; by expression of a recombinant nucleic acid; or by chemically synthesizing the polypeptide. Purity is measured by a number of methods known in the art, e.g., column chromatography, polyacrylamide gel electrophoresis, or HPLC analysis. A protein is substantially free of naturally associated components when it is separated from those contaminants, which accompany it in its natural state. Thus, a protein, which is chemically synthesized or produced in a cellular system different from the cell from which it naturally originates, is substantially free from its naturally associated components.

The term peptide is used interchangeably with polypeptide in the present specification to designate a series of amino acids connected one to the other by peptide bonds between the alpha-amino and alpha-carboxy groups of adjacent amino acids. Optionally, one or more peptide bonds are replaced with an alternative type of covalent bond (a "peptide mimetic"), which is not susceptible to cleavage by peptidases. Where proteolytic degradation of the peptides following injection into the subject is a problem, replacement of a particularly sensitive peptide bond with a non-cleavable peptide mimetic yields a peptide mimetic, which is more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as pyroglutamate, t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. The polypeptides or peptides are either in their neutral (uncharged) forms or in forms, which are salts. Polypeptides are either free of post-translational modifications such as glycosylation, side chain oxidation, or phosphorylation or contain such modifications, subject to the condition that the modification does not destroy the biological activity, e.g., anti-angiogenesis or induction of apoptosis, of the polypeptides.

Derivative peptides are also within the invention, provided that the derivation peptide retains a biological activity e.g., anti-angiogenesis or induction of apoptosis, of a polypeptide consisting essentially of SEQ ID NO:1, 2, 3, or 4. The derivative contains a conservative amino acid substitution. By conservative substitutions is meant replacing an amino acid residue with another, which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr.

Also within the invention is a method of reducing tumor burden in a mammal. The method is carried out by delivering to and contacting a tumor cell or mass with a composition containing fragment of an antineoplastic urinary protein polypeptide which is at least 20 amino acids in length and comprises the amino acid sequence of SEQ ID NO:1, 2, 3, or 4 and which induce apoptosis in tumor cell. Tumor burden is preferably reduced by at least 10%, 20%, 30%, 40%, 50%, 70%, 100% and up to 200% or more compared to an untreated tumor. The method optionally includes the step of further administering to the mammal a non-peptide chemotherapeutic agent, e.g., methotrexate or vinblastin, or a peptide therapeutic such as Herceptin, Rituxan and Tarceva.

Other embodiments and features of the invention will be apparent from the following description thereof, and from the claims.

BRIEF DESCRIPTION OF THE DRAWINGS

FIGS. 1A-C are a series of graphs showing inhibition of HeLa tumor growth by ANUP peptides in nude mice. Five million Hela cells were transplanted per mouse. After 3 days, mice were treated with Pep A (500 μg and 750 μg), Pep B (500 μg) or buffer only (200 μL volume; PBS+0.05% SDS) on days 3, 6, 10 and 13 (arrows). Tumor growth was measured three times per week and mice were sacrificed on day 24 post transplantation.

FIGS. 3A-D are a series of photomicrographs showing inhibition of bFGF-mediated angiogenesis in early chick embryos by ANUP Peptides. The micrographs show induction of angiogenesis resulting from the topical administration of 100 ng of bFGF on the CAM of day-10 chick embryos.

FIGS. 4A-B are photomicrographs showing resected CAM tissues topically treated with 100 ng bFGF in the presence of Pep A and fluorescently labeled to analyze for apoptosis. Apoptotic nuclei intensely stain with H-33342 (and appear white) under epifluorescence visualization compared to viable cells (blue nuclei).

FIG. 4A shows the results of treatment with 100 ng bFGF plus 200 ng Pep A (100× magnification). Intensely staining apoptotic nuclei (white) of vascular cells resulted in the outlining of the vessels against the lighter stained non-vascular cell nuclei.

FIG. 5A-B are photomicrographs showing histopathology of tumors isolated from control mice.

DETAILED DESCRIPTION

Significant progress has been made in the battle against cancer; however, it still ranks as the second leading cause of death in the United States behind cardiovascular disease. Chemotherapeutic agents have demonstrated good efficacy when the cancer is detected early, but have proven primarily palliative against late stage cancers. New therapies are focusing on multifaceted approaches to starve and kill tumors utilizing both anti-angiogenic and chemotherapeutic compounds. The anticancer peptides described herein reduced tumor burden by up to 70% in a nude mouse model and demonstrated the ability to inhibit blood vessel formation.

ANUP Peptides

ANUP is a naturally occurring dimer of 32 kD that has been characterized for its activity against various tumor types. Two twenty amino acid peptides complementary to the N-terminal sequence of antineoplastic urinary protein (ANUP) were characterized. ANUP was originally identified as a 32 KD dimer in human urine by Sloane et al. (N. H. Sloane et al., Biochem. J. 234, 355 (1986)). ANUP inhibited endothelial cell migration and tumor cell proliferation, as well as demonstrated anti-angiogenic properties by inhibition of bFGF- and VEGF-mediated blood vessel growth in chick chorioallantoic membrane (CAM) assays (R. Masood et. al. Blood 93(3), 1038, (1999)). ANUP possessed an N-terminal pyroglutamate blockage and complex solubilization and solution properties that indicated conformational requirements for activation of the molecule. The N-terminal region of ANUP had been previously identified as the active region using a synthetic nonapeptide (N. H. Sloane & L. H. Davis, Tumor Targeting 2, 322 (1996)). A larger peptide was found to provide sufficient activity, ease of production, and improved delivery options, facilitating its use in a clinical setting. The two peptides, Peptide A (Pep A; ELKCYTCK-EPMTSASCRTIT; SEQ ID NO:1) and Peptide B (Pep B; pyroELKCYTCKEPMTSASCRTIT; SEQ ID NO:2), differ only by the nature of the N-terminal amino acid. Pep B has an N-terminal pyroglutamate blockage, while Pep A contains an N-terminal glutamine. In Pep B, the N-terminal Glu is cyclized with the amino group displacing the amide amino to form a pyroglutamate moiety, a form that lacks a —$NH_2$ group. The peptides were chemically synthesized and purified using standard methods. The peptides were tested both in vivo (nude mice) and in vitro (using embryonic neovascularization, CAM, and cell proliferation assays). The following 20-mer peptides were also made: E-L-K-C-Y-T-C-K-E-P-M-T-S-A-A-C-R-T-I-T (SEQ ID NO:3) and Pyroglutamic Acid-L-K-C-Y-T-C-K-E-P-M-T-S-A-A-C-R-T-I-T (SEQ ID NO:4). Shorter peptides of 6, 7, 8, 9, 10, 11, 12, 13, 14, 15, 16, 17, 18, and 19 amino acids are synthesized, purified, and administered in the same manner. Shorter peptides contain the amino acid sequence consisting of therefor (residues 5-10 of SEQ ID NO:1, 2, 3, or 4

The data described herein were generated using the following reagents and methods.

Peptide Synthesis

ANUP peptides such as those that contain the amino acid sequence of SEQ ID NO:1, 2, 3, or 4, and fragments thereof, such as a 6 mer containing residues 5-10 of each of the above-referenced sequences were synthesized by SynPep Corporation (Dublin, Calif.) to >70% purity.

Chicken Chorioallantoic Membrane (CAM) Assay

The chicken chorioallantoic membrane (CAM) assay was completed to assess the effect of the peptides on basic fibroblast growth factor (bFGF) induced angiogenesis. Small windows were created through the blunt end of the shell directly over the air sac of 9-10 day old White Leghorn chick embryos with the use of a small crafts Dremel drill. The air sac was peeled-off, and filter disks saturated with basic fibroblast growth factor (bFGF) and the test peptide (or buffer control) were placed adjacent to each other on the CAM of the chick embryo. The shell windows were sealed with parafilm and eggs were incubated at 37° C. in a humidified egg incubator. After 48-72 hours, the CAM tissue directly below the filter disks was resected. Tissues were washed three times with PBS and analyzed using a stereomicroscope. The number of branching blood vessels infiltrating under the filter disks were determined and documented.

Chick Embryo Neo-Vascularization Inhibition Assay

This assay was completed to determine the impact of Pep A and Pep B on neo-vascularization of early chick embryo. Small windows were created through the blunt end of the shell directly over the air sac of 3.5-day old White Leghorn chick embryos with the use of a small crafts Dremel drill. The air sac was peeled-off and filter disks with different concentrations of the test peptide or buffer control were placed over a section of the developing blood ring and overlapping connecting vessels of the chick embryo. The shell windows were sealed with parafilm and eggs were incubated at 37° C. in a humidified egg incubator. After 48-72 hours, the yolk membrane tissue directly below the filter disks was resected. Tissues were washed three times with PBS and analyzed for inhibition of neo-vascularization using a stereomicroscope with photo-digital attachment.

Detection of Cell Death

A dual fluorescent staining procedure (H-33342 and Propidium Iodide, 5 µg/ml) was used to differentially determine the incidence of apoptosis and necrosis of the resected tissues. The staining procedure was carried out using known methods, e.g., the methods described in (Baguisi et al., Annual Conference of the International Embryo Transfer Society. Quebec City, Quebec, Canada. Jan. 10-12, 1999. Proceedings and abstracts. Theriogenology January 1; 51(1): 1-448 (1999)). Following staining, the tissues were washed three times in PBS and fixed in 4% formalin. The tissues were visualized under epifluorescence using a photo-digital imaging system. The number of live, apoptotic and necrotic cells were determined.

Tumor Cell Culture and Harvesting

The HeLa human cervical cancer cell line (ATCC, Manassas Va.; CCL-2) was grown according to direction in DMEM containing 10% fetal bovine serum. Cells in log phase were harvested from flasks using trypsin-EDTA (0.25% trypsin/1 mM Na-EDTA; Invitrogen), washed in PBS and resuspended in DMEM for counting and viability assessment using trypan blue exclusion. Viability and re-plating efficiency were greater than 98% and 95% respectively. Cells were resuspended at $5 \times 10^7$ cells/mL in PBS for injection into the mice.

In Vivo Nude Mice Experiment

Nude nu/nu mice (4 to 5 week-old females) were acclimated for 1 week and injected with 5 million HeLa cells subcutaneously (SQ) in a total volume of 100 µL. After 3 days of tumor development, the mice were injected SQ with each peptide prepared in phosphate buffered saline (PBS) containing 0.05% sodium dodecyl sulfate (SDS) or PBS+ 0.05% SDS alone. All doses were 200 µL in volume, with additional treatments on days 6, 10 and 13 post-transplantation. Treatments were alternated between flanks of the mice. Tumor size and mouse weights were measured three times per week. The results represent the average of the 3 mice in each group. The experiment was terminated on day 24 and the tumors were excised for weight and histopathology.

The following Human Umbilical Vein Endothelial Cells (HUVEC) assays, which have been set up by the Developmental Therapeutics Program NCI/NIH, are also used for evaluate anti-angiogenic activity. The anti-angiogenic compounds, TNP-470 (NSC 642492) and paclitaxel (NSC 125973), are used as reference compounds (positive controls) in the art-recognized assays described below.

Growth Inhibition Assay

HUVEC ($1.5 \times 10^3$) are plated in a 96-well plate in 100 µl of EBM-2 (Clonetic # CC3162). After 24 h (day 0), the test compound (100 µl) is added to each well at 2× the desired concentration (5-7 concentration levels) in EBM-2 medium. On day 0, one plate is stained with 0.5% crystal violet in 20% methanol for 10 minutes, rinsed with water, and air-dried. The remaining plates are incubated for 72 h at 37° C. After 72 h, plates are stained with 0.5% crystal violet in 20% methanol, rinsed with water and air-dried. The stain is eluted with 1:1 solution of ethanol:0.1 M sodium citrate (including day 0 plate), and absorbance is measured at 540 nm with an ELISA reader (Dynatech Laboratories). Day 0 absorbance is subtracted from the 72 h plates and data is plotted as percentage of control proliferation (vehicle treated cells). $IC_{50}$ (drug concentration causing 50% inhibition) is calculated from the plotted data.

Cord Formation Assay

Matrigel (60 μl of 10 mg/ml; Collaborative Lab #35423) is placed in each well of an ice-cold 96-well plate. The plate is allowed to sit at room temperature for 15 minutes then incubated at 37° C. for 30 minutes to permit the matrigel to polymerize. In the mean time, HUVEC are prepared in EGM-2 (Clonetic #CC3162) at a concentration of $2 \times 10^5$ cells/ml. The test compound is prepared at 2× the desired concentration (5 concentration levels) in the same medium. Cells (500 μl) and 2× drug (500 μl) is mixed and 200 μl of this suspension are placed in duplicate on the polymerized matrigel. After 24 h incubation, triplicate pictures are taken for each concentration using a Bioquant Image Analysis system. Drug effect ($IC_{50}$) is assessed compared to untreated controls by measuring the length of cords formed and number of junctions.

Cell Migration Assay

Migration is assessed using the 48-well Boyden chamber and 8 μm pore size collagen-coated (10 μg/ml rat tail collagen; Collaborative Laboratories) polycarbonate filters (Osmonics, Inc.). The bottom chamber wells receive 27-29 μl of DMEM medium alone (baseline) or medium containing chemo-attractant (bFGF, VEGF or Swiss 3T3 cell conditioned medium). The top chambers receive 45 μl of HUVEC cell suspension ($1 \times 10^6$ cells/ml) prepared in DMEM+1% BSA with or without test compound. After 5 h incubation at 37° C., the membrane is rinsed in PBS, fixed and stained in Diff-Quick solutions. The filter is placed on a glass slide with the migrated cells facing down and cells on top are removed using a Kimwipe. The testing is performed in 4-6 replicates and five fields are counted from each well. Negative unstimulated control values are subtracted from stimulated control and drug treated values and data is plotted as mean migrated cell±S.D. $IC_{50}$ is calculated from the plotted data.

Reduction of Tumor Burden

To assess the potential for inhibition or reduction of tumor burden by the peptides, their activity was examined using an active treatment nude mouse model of human cervical cancer. HeLa cells ($5 \times 10^6$ cells in 100 μL were administered subcutaneously (SQ). The cells were implanted in the left mid-flank region of 5 week old immunodeficient Nude nu/nu female mice (Charles River Labs, Wilmington, Mass.) and allowed to develop to palpable size (average diameter=3.9 $mm^2$; average volume=24 $mm^3$). Mice were randomized and divided into experimental groups, with 3 mice per group. The mice were treated with SQ injections (200 μL) of various doses of peptide in phosphate buffered saline (PBS) containing a detergent, e.g., 0.05% sodium dodecyl sulphate (SDS). Control mice were injected with PBS containing 0.05% SDS alone. The presence of SDS was required for activation of the activity in the nonapeptide and the protein. The treatments were administered on days 3, 6, 10 and 13 post-transplantation. Tumors were measured three times per week until the experiment was terminated on day 24 post-transplantation.

Figure 1A:
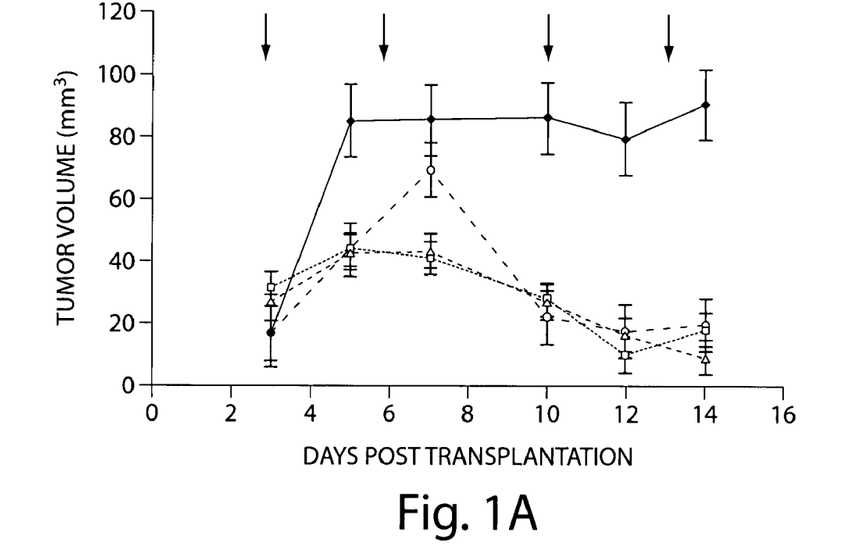
FIG. 1A is a line graph showing inhibition of HeLa tumor growth during treatment phase. Results represent the average tumor volume of all mice (n=3). Treatments with Pep A at 500 μg per dose (open square), Pep A at 750 μg per dose (open triangle) and Pep B (open circle) all demonstrate tumor inhibition during the treatment phase while control tumors (solid diamond) remain static.
Figure 1B:
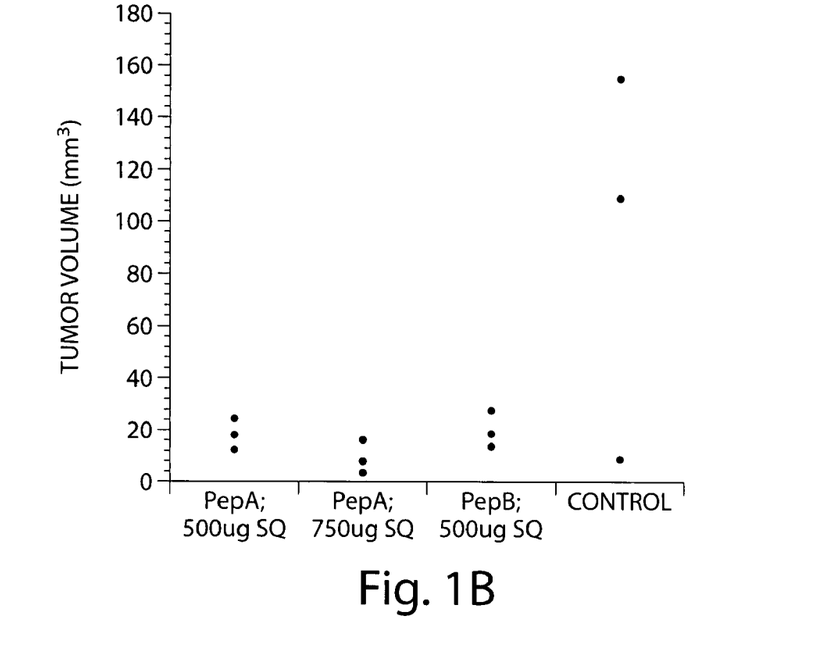
FIG. 1B is a scatter plot graph showing the response of individual tumors to treatment with peptides. Tumors were measured on day 14 (one day post last treatment). Individual mice tumor volumes demonstrate response of all animals treated with either Pep A or Pep B.
Figure 1C:
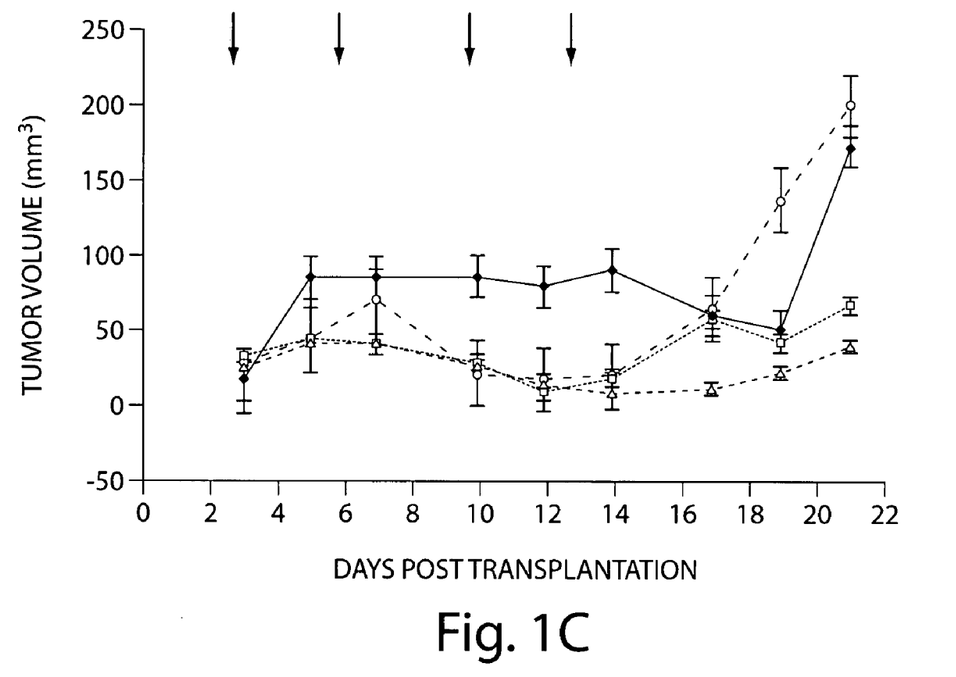
FIG. 1C is a line graph showing tumor growth profiles post treatment with Pep A and Pep B. A slight increase in tumor burden was noted for both Pep A treatment groups and escalation of tumor burden in the control and Pep B treated groups subsequent to the fourth treatment. Symbols are as described for FIG. 1A.

All groups demonstrated an initial inhibition of tumor growth compared to the control group (FIG. 1A, B). The inhibition continued with some decrease in tumor volume seen in most groups after the second treatment. This trend continued during the treatment phase but was lost shortly after treatment stopped for Pep B, while both doses of Pep A had only limited tumor growth for the duration of the experiment (FIG. 1C). In the control group, tumor growth was initially rapid followed by a 10-14 day stationary period and then a renewed rapid tumor growth until experiment termination (FIG. 1C). Animal weights continued to rise during the treatment phase and there were no adverse events associated with the treatments. Earlier work with ANUP protein demonstrated a similar profile for both HeLa tumors (N. H. Sloane & L. H. Davis, Tumor Targeting 2, 322 (1996)) and Karposi's sarcoma tumors (R. Masood et. al. Blood 93(3), 1038, (1999)) in nude mice as that demonstrated for Pep B in this experiment with renewed growth of tumors after the treatment phase.

Figure 5A:
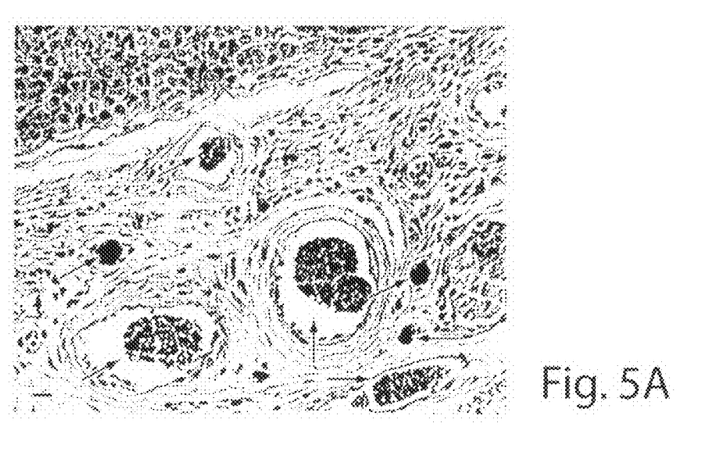
FIG. 5A shows neo-vascularization of the tumor from a control mouse. Areas of blood vessel growth (solid arrows) proximate to the tumor.
Figure 5B:
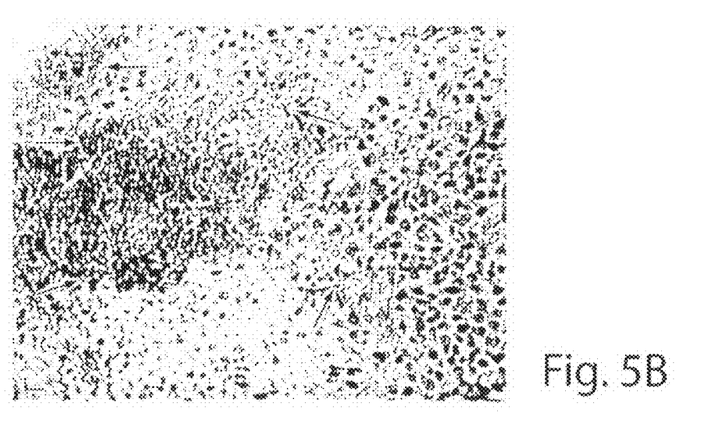
FIG. 5B shows infiltration of blood vessels in the tumor from a control mouse. Vessels infiltrating into tumor (solid arrowheads). Darkly pigmented nuclei indicate areas of cell death (e.g. double lined arrows).
Figure 5C:
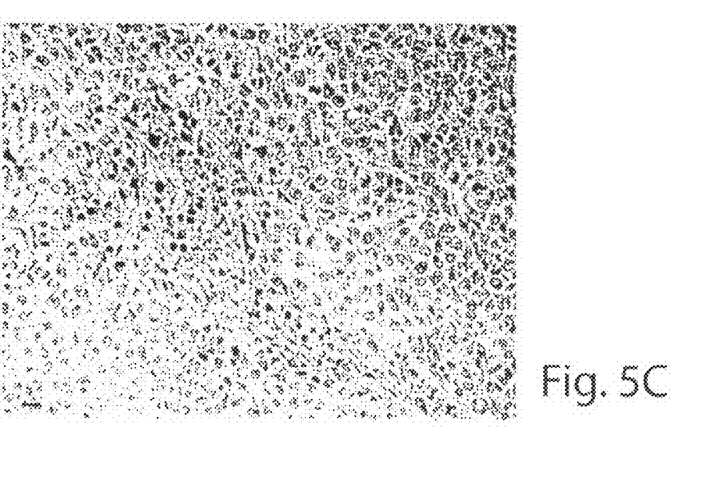
FIG. 5C shows larger areas of cell death in tumors isolated from Pep A treated mice are evident by the increased number of dark nuclei. Magnification, 75×; scale bars, 10 μm.

Tumors were isolated upon sacrifice and prepared for histopathology. The isolated tumors revealed significantly less vascularization and infiltration from the Pep A and Pep B treated mice compared to control mice ((FIG. 5A-C). The areas of cell death in the tumors from the Pep A high dose group were also noticeably larger than those of the other groups.

Inhibition of Tumor Cell Growth

Figure 2:
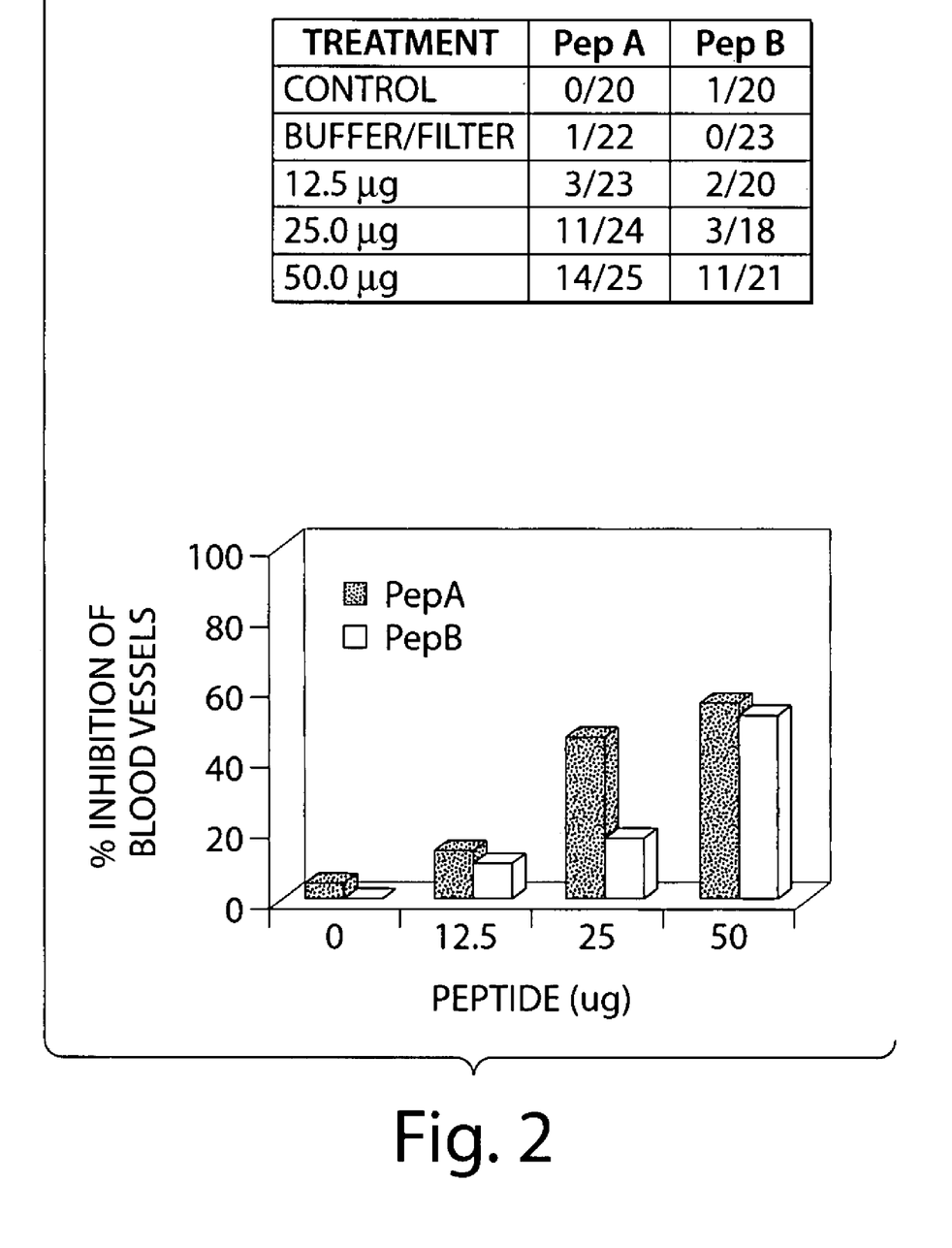
FIG. 2 is a bar graph showing dose dependent suppression of branching vessel formation on day-3.5 chick embryo by Pep A and Pep B. A single topical dose induced the suppression of branching vessel formation and development. Pep A showed inhibition beginning at 25 μg versus Pep B which showed inhibition by 50 μg. The number of embryos treated is indicated on the table on the left.
Figure 3A:
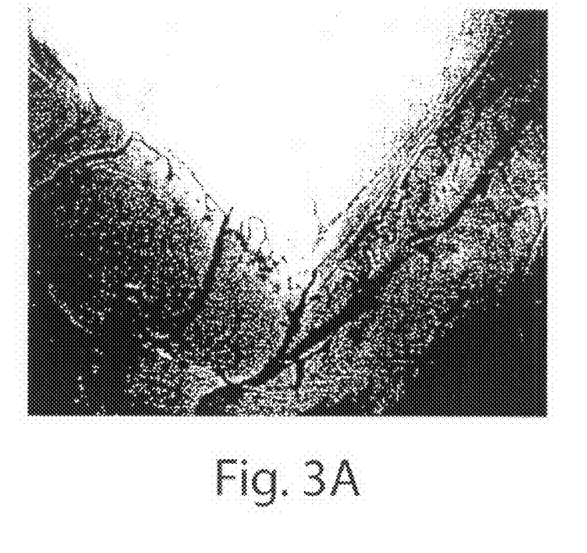
FIGS. 3A-B are photomicrographs showing neo-vascularization along the edges of the filter disks and vascular infiltration, respectively, after administration of bFGF alone.
Figure 3B:
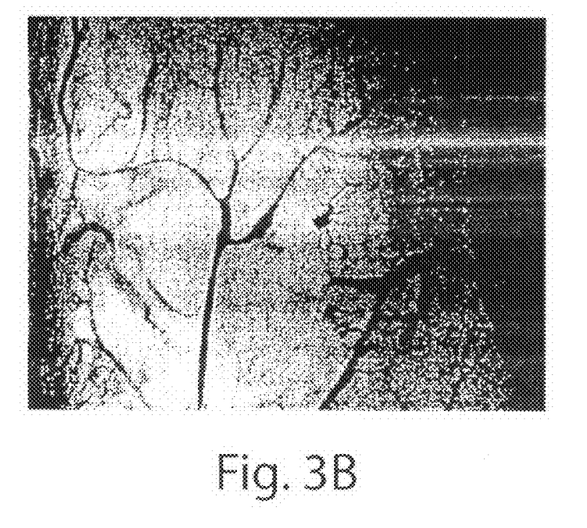
Figure 3C:
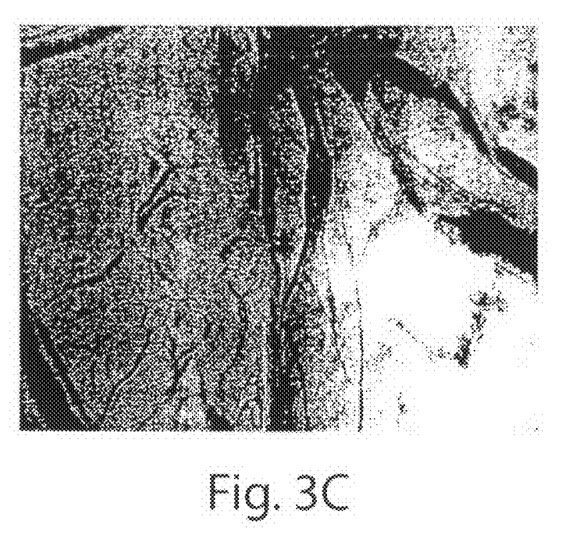
FIG. 3C is a photomicrograph showing that inhibition of neo-vascularization and infiltration as well as degradation of pre-existing vessels is demonstrated by co-administration of 200 pg Pep A with 100 ng bFGF.
Figure 3D:
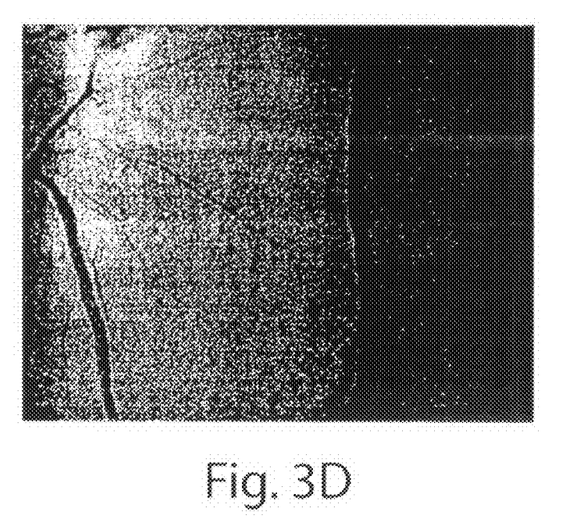
FIG. 3D is a photomicrograph showing that co-administration of 200 ng Pep B with 100 ng bFGF results in inhibition of bFGF-induced angiogenesis.

Studies were conducted to elucidate the mechanism of action for the peptides. Antiproliferative potential was assessed in standard neutral red and MTT assays on several human tumor cells and demonstrated little or limited activity at doses up to 2 mg/mL. Inhibition of neo-vascularization was investigated by administration of Pep A and Pep B on the proliferating blood vessels of day 3.5 chick embryos using filter disks saturated with test peptide or buffer control. Both peptides selectively suppressed or delayed neo-vascularization in a dose dependent manner (FIG. 2). At a dose of 25 μg for Pep B and 50 μg for Pep A, the peptides disrupted and delayed capillary vessel development as well as reduced the growth of pre-existing vessels without affecting pre-existing blood vessels adjacent to the disks. At a dose of 100 μg, both peptides showed identical antiangiogenesis activity, comparable to the effects observed at 50 μg. In contrast to the peptides, the buffer control had no observable effects. The viability of the embryos was not affected by any of the treatment regimens.

Inhibition of Blood Vessel Formation

Inhibition of bFGF-induced angiogenesis in a CAM assay is another hallmark of antiangiogenesis. Ten day old chick embryos were exposed to increasing doses of either Pep A or Pep B in the presence of 100 ng or 200 ng of basic fibroblast growth factor (bFGF) for 48 hours at 37° C. 200 ng of either peptide suppressed the angiogenesis activity induced by 100 ng of bFGF, with Pep A showing comparatively better inhibition of blood vessel infiltration than the Pep B (FIG. 3). At a dose of 200 ng of bFGF, only Pep A showed suppression. The formation of branching vessels and smaller capillary vessels were inhibited by both peptides. Closer examination of the effects of the peptides on angiogenesis revealed the presence of discontinuous and disrupted blood vessels. These data indicate that ANUP peptides Pep A and Pep B, inhibited angiogenesis. Pep A was found to be a more potent anti-angiogenic agent.

Figure 4A:
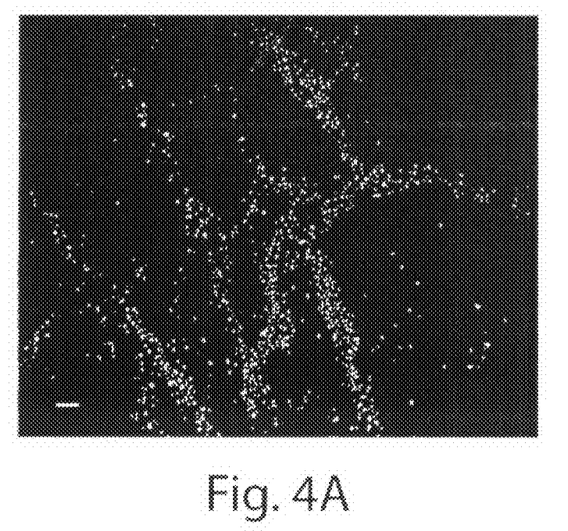
Figure 4B:
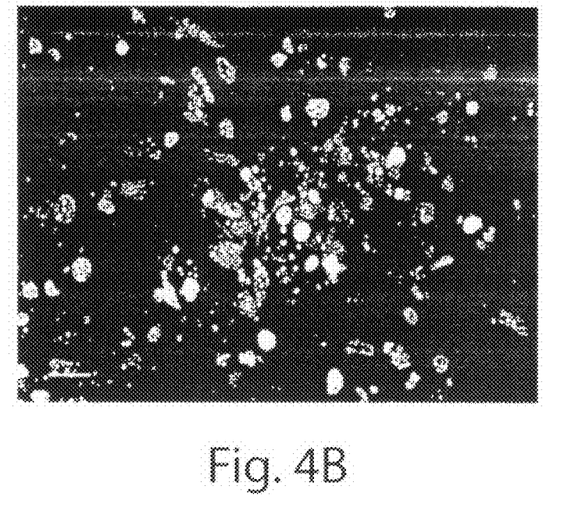
FIG. 4B shows the field at higher magnification (200× magnification), and the cells were confirmed to be apoptotic. The Pep B-treated CAM did not demonstrate the perivascular apoptosis and the white nuclei were randomly distributed throughout the CAM tissue. As expected, bFGF treated control CAM did not demonstrate apoptosis.

To identify the mechanism of action of the peptides, the resected CAM tissues were dually labeled with fluorescent stains to show evidence of cell demise through either lysis or apoptosis. Minimal levels of lysed cells (stained with propidium iodide) were observed on the tissues treated with the peptides and were similar to that observed on the bFGF treated controls. There was however, a significant increase in DNA fragmentation on CAM tissues treated with Pep A as compared to either Pep B or bFGF control after staining with H-33342. Intensely staining apoptotic bodies were seen in tissues from the Pep A treated CAMs and were localized on the vascular cells. This resulted in outlining of the vessels against the non-vascular tissues (FIG. 4). Pep B showed minimal increase in apoptosis over the control, with a random staining pattern observed. However, there was an observable condensation of the cell nuclei in the Pep B treated CAMs as compared to controls. Peri-vascular apoptotic cells have previously been demonstrated in mouse carcinomas using the antiangiogenic compounds Fc-angiostatin and Fc-endostatin where the combination of these compounds resulted in significant reduction of tumor volume (G. Bergers et al., Science 284, 808 (1999)). These data indicate that PepA induces cell death by apoptosis.

ANUP Peptides Reduce Osteosarcoma Tumor Load in an Animal Model

The 20mer ANUP peptide, SEQ ID NO:1 (MW=2265.6) and the 6 mer peptide (MW=740.0; residues 5-10 of SEQ ID NO:1), were synthesized and HPLC purified by SynPep Corporation (Dublin, Calif.) to >70% purity.

The ANUP P16/21 protein pool was purified from human plasma. Thawed samples were adjusted to approximately pH 5.0 and then subjected to Florosil column step chromatography (pH 4.0 followed by pH 8.8-9.0 elution). The florosil eluate was applied to a DEAE column at 10 mg total protein per mL resin for subsequent elution in high salt. The DEAE eluate was then concentrated and applied to a Superdex-200 size chromatography column. Fractions were visualized by SDS-Page and Western analysis prior to pooling to provide the material used in the animal experiment.

Tumor cell culture and harvesting was carried out as follows. Human osteogenic sarcoma cancer cells (OSRC cell line) was grown in DMEM containing additional non-essential amino acids and vitamins and 10% heat inactivated fetal bovine serum (Invitrogen™, Carlsbad, Calif.). Cells in log phase were harvested from flasks using trypsin-EDTA (0.05% trypsin/0.53 mM Na-EDTA; Invitrogen™), washed in PBS and resuspended in DMEM for counting and viability assessment using trypan blue exclusion. Cells were resuspended at $2.5 \times 10^7$ cells per ml in PBS for injection into the mice.

Figure 6A:
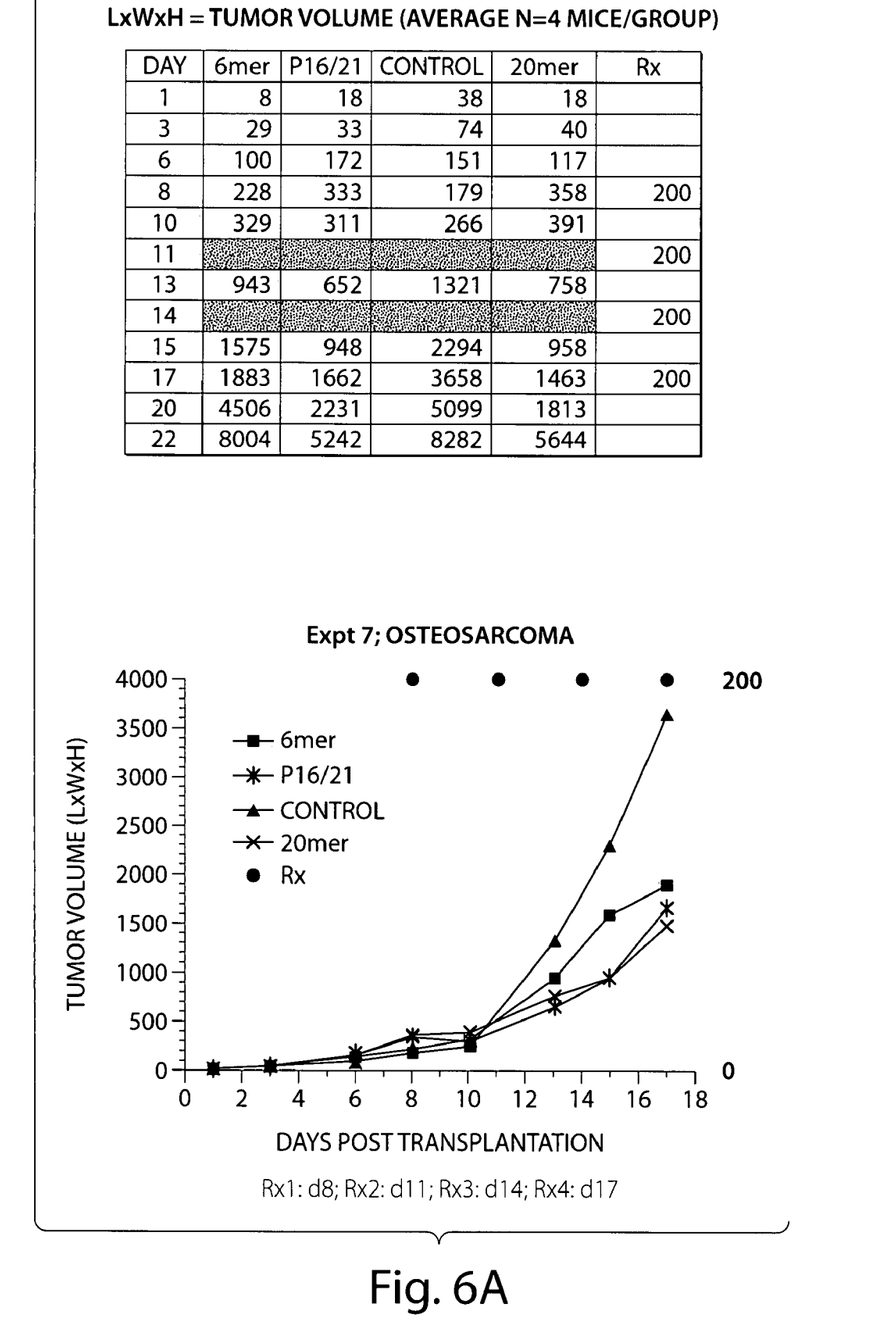
FIGS. 6A-B are bar graphs showing reduction of osteosarcoma tumor volume in mice following administration of ANUP peptides. 6 mer designates residues 5-10 of SEQ ID NO:1, 20-mer designates SEQ ID NO:1, and P16/21 designates an ANUP protein pool purified from plasma (contains 16 kDa and 21 kDa proteins).
Figure 6B:
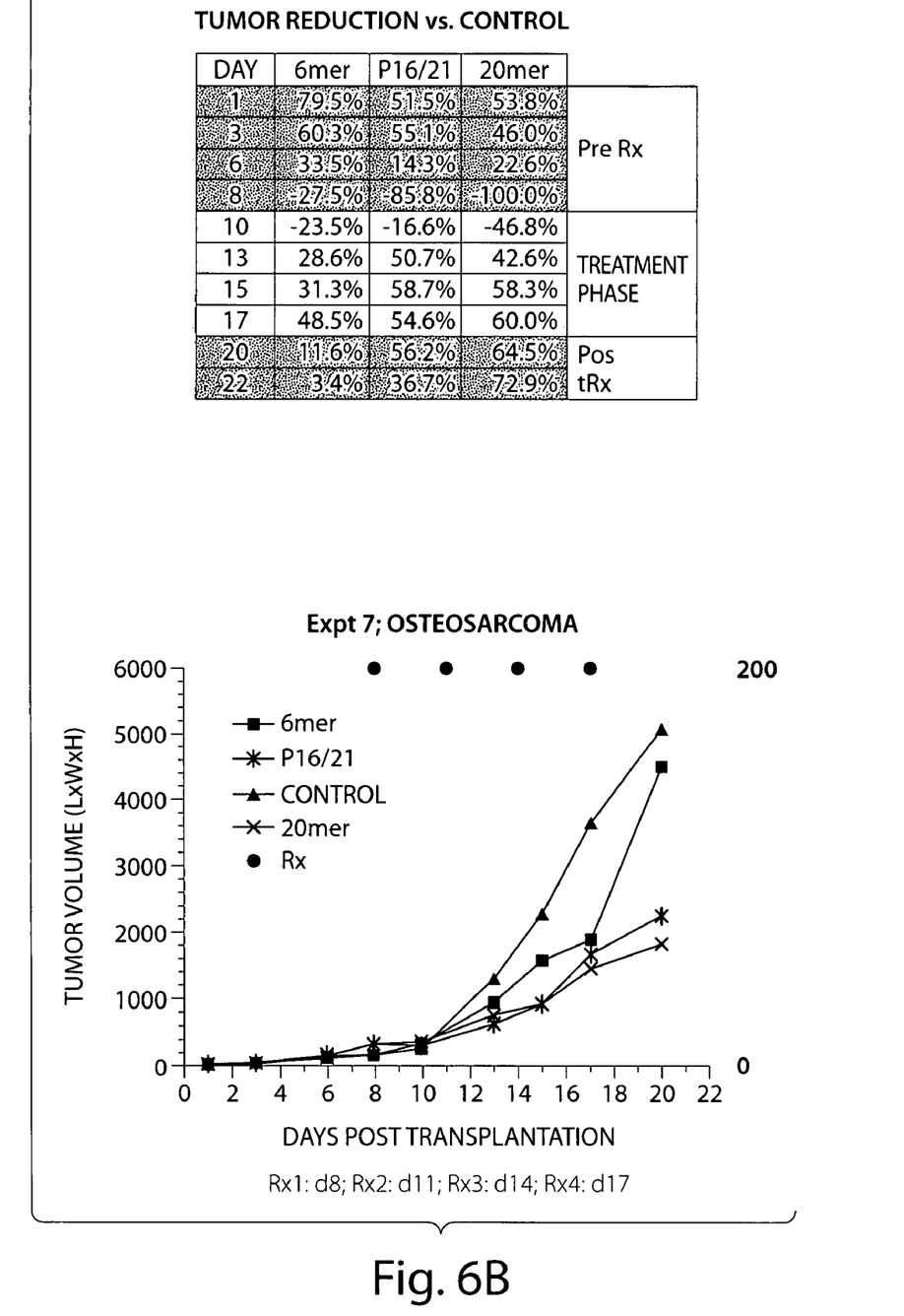

Nude nu/nu mice (4 to 5 week-old females, Charles River Labs, Wilmington, Mass.) were acclimated for 1 week before injection with 2.5 million OSRC cells subcutaneously (SQ) in a total volume of 100 µl. After 8 days of tumor development, the mice were injected SQ with each peptide or the protein pool prepared in phosphate buffered saline (PBS) containing 0.05% sodium dodecyl sulfate (SDS) or PBS+0.05% SDS alone (Control). All doses were 200 µl in volume, with additional treatments on days 11, 14 and 17 post-transplantation. Treatments were alternated between flanks of the mice. Tumor size (length, width and height) and mouse weights were measured three times per week. The results (FIGS. 6A-B) represent the average of the 4 mice in each group. The table above the graphs (FIGS. 6A-B) show the treatment schedule; the last treatment day was on Day 17. At the end of the experiment, the mice were terminated and the tumors were excised for weight and histopathology.

These data indicate that tumor burden (e.g., as measured by tumor volume) in an animal is reduced by treating the animals with ANUP peptides. When administration of ANUP peptides is stopped, the tumors were observed to increase in size. These data indicate a treatment schedule of regular or continuous administration of the peptide reduces tumor mass.

Therapeutic Administration

ANUP is a member of a growing class of antiangiogenic and antitumor substances that are derived from the proteolysis or other modification of blood proteins. Other proteins in this group include heparin-binding fragments of fibronectin (G. A. Homandberg et. al., Am. J. Pathol. 120, 327 (1985); G. A. Homandberg et. al., Biochim. Biophys. Acta 874, 61 (1986)), modified antithrombin (M. S. O'Reilly et. al., Science 285, 1926 (1999), angiostatin (M. S. O'Reilly et. al., Cell 79, 315 (1994), and endostatin (M. S. O'Reilly et. al., Cell 88, 277 (1997)). The other proteins listed above are known to bind to adhesion proteins, and ANUP demonstrated inhibition of cell migration. ANUP also effects endothelial cell migration by binding to a cell surface receptor in this lineage (R. Masood et. al. Blood 93(3), 1038, (1999)). \In cell culture, the ANUP protein, but not the peptides, demonstrated antiproliferative effects on a wide variety of human tumor cells. The data indicate that the antiangiogenic region resides in the N-terminal 20 amino acids since angiogenesis is not a requirement for the proliferation of tumor cells in culture, while the antiproliferative activity for the protein resides elsewhere in the molecule or is dependent upon conformational changes not possible with the peptides. Pep B requires activation by removal of the pyroglutamate molecule in order to obtain full activity by either conformational changes or binding site interaction requirements. The ability of both forms of the peptide to inhibit neovascularization of chick embryos as well as to inhibit angiogenesis in bFGF mediated CAM assays indicates that the N-terminus contains the antiangiogenic activity for the molecule.

ANUP peptides are administered in the form of a peptide solution in a pharmaceutically acceptable carrier. Such methods are well known to those of ordinary skill in the art. The peptides are administered at an intravenous dosage of approximately 1 to 100 µmoles of the polypeptide per kg of body weight per day. For example, peptides are administered, daily, every other day, weekly, or monthly. In another example, the peptides are administered continuously such as by an erodible implant or peptide impregnated patch. The compositions of the invention are useful for parenteral administration, such as intravenous, subcutaneous, intramuscular, intraperitoneal, or directly into or onto a tumor site. The compositions are also administered orally. A unit dose of the peptide ranges from 0.1 to 100 mg, which may be administered at one time or repeatedly to a patient. A plurality of peptides are optionally administered together (simultaneously or sequentially).

Peptides are recombinantly produced or synthetically made using known methods. Peptide solutions are optionally lyophilized or granulated with a pharmaceutically acceptable vehicle. When the compositions are administered by injection, they are dissolved in distilled water or another pharmaceutically acceptable excipient prior to the injection. ANUP peptides are optionally administered in combination with other therapeutic modalities, such as Herceptin, Rituxan and Tarceva. Combination therapies include ANUP Pep A with other anti-cancer molecules. An ANUP peptide is optionally modified by linking it with another chemotherapeutic agent. ANUP Pep A was shown to possess antiangiogenesis activity both in vitro and in vivo.

Other embodiments are within the following claims.

What is claimed is:

1. A method of inhibiting blood vessel formation in a tissue, comprising contacting said tissue with a fragment of an antineoplastic urinary protein polypeptide, wherein said fragment consists of SEQ ID NO: 1, 2, 3 or 4.

2. The method of claim 1, wherein said fragment consists of SEQ ID NO: 1.

3. The method of claim 1, wherein said fragment consists of SEQ ID NO: 2.

4. The method of claim 1, wherein said tissue comprises a tumor cell.

5. A method of reducing tumor burden in a mammal, comprising contacting a tumor mass with a composition comprising a fragment of an antineoplastic urinary protein polypeptide, wherein said fragment consists of SEQ ID NO: 1 or 2.

6. The method of claim 5, wherein said fragment consists of SEQ ID NO: 1.

7. The method of claim 5, wherein said fragment consists of SEQ ID NO: 2.

8. The method of claim 5, further comprising administering to said mammal a non-peptide chemotherapeutic agent.

9. A method of reducing tumor burden in a mammal, comprising contacting a tumor mass with a composition comprising a fragment of an antineoplastic urinary protein polypeptide, wherein said fragment consist of residues 5-10 of SEQ ID NO: 1.

* * * * *